(12) United States Patent
Ciupik et al.

(10) Patent No.: US 8,753,400 B2
(45) Date of Patent: Jun. 17, 2014

(54) PROSTHESIS OF ANTERIOR SPINAL COLUMN, INSTRUMENT GUIDING THE PROSTHESIS AND METHOD FOR INSTALLATION THEREOF

(75) Inventors: Lechoslaw Ciupik, Zielona Gora (PL); Pawel Powchowicz, Zielona Gora (PL); Ely Ashkenazi, Jerulsalem (IL)

(73) Assignee: LfC Sp. z o.o., Zeilona Gora (PL)

( * ) Notice: Subject to any disclaimer, the term of this patent is extended or adjusted under 35 U.S.C. 154(b) by 378 days.

(21) Appl. No.: 13/027,958

(22) Filed: Feb. 15, 2011

(65) Prior Publication Data
US 2011/0218628 A1 Sep. 8, 2011

(30) Foreign Application Priority Data

Mar. 3, 2010 (PL) .......................................... 390601

(51) Int. Cl.
*A61F 2/44* (2006.01)
(52) U.S. Cl.
USPC ..................................... 623/17.16; 623/17.11
(58) Field of Classification Search
USPC ........................................... 623/17.11–17.16
See application file for complete search history.

(56) References Cited

U.S. PATENT DOCUMENTS

| | | | |
|---|---|---|---|
| 2003/0004576 A1 | 1/2003 | Thalgott | |
| 2006/0030857 A1 | 2/2006 | DeVilliers et al. | |
| 2007/0270873 A1 | 11/2007 | Flickinger et al. | |
| 2008/0221694 A1* | 9/2008 | Warnick et al. | 623/17.16 |
| 2009/0164017 A1* | 6/2009 | Sommerich et al. | 623/17.16 |
| 2009/0164019 A1* | 6/2009 | Hsu et al. | 623/17.16 |
| 2009/0276050 A1* | 11/2009 | Biedermann et al. | 623/17.16 |
| 2010/0094422 A1* | 4/2010 | Hansell et al. | 623/17.16 |
| 2010/0094424 A1* | 4/2010 | Woodburn et al. | 623/17.16 |
| 2011/0098820 A1* | 4/2011 | Blackwell et al. | 623/17.16 |

FOREIGN PATENT DOCUMENTS

| | | |
|---|---|---|
| DE | 4328690 A1 | 3/1995 |
| DE | 202005007809 U1 | 7/2005 |
| EP | 0968692 A1 | 1/2000 |
| EP | 1188424 A1 | 3/2002 |

(Continued)

OTHER PUBLICATIONS

International Preliminary Report on Patentability; Reported Issued on Sep. 4, 2012 re International Application No. PCT/PL2011/000013; Intl. filing date—Feb. 11, 2011; Priority date—Mar. 3, 2010.

(Continued)

*Primary Examiner* — Todd Manahan
*Assistant Examiner* — Jessica Weiss
(74) *Attorney, Agent, or Firm* — Hovey Williams LLP

(57) ABSTRACT

A prosthesis of an anterior spinal column, comprising a perforated sleeve body (1) with at least one anchoring element, teeth and overgrowth holes and a positioner (2) situated within the body (1). The body (1) has in its wall at least one manipulative hole (6) and at least one positioning hole (7), whose longitudinal axes are parallel with each other. The positioner (2) comprises at least one situating element (8) cooperating with at least one positioning hole (7) of the body (1) and at least one hole (12) formed therethrough, which may be situated radially inward relative to the manipulative hole (6). At least one end face (3) of the body (1) or/and body's wall are provided with at least one pair of opposite guidelines (14,20). For introducing the prosthesis into the intervertebral space, a guiding instrument is used in the form of a rod with a shaped working element (24) at one end. The prosthesis may be implanted with the use of the prosthesis guiding instrument.

24 Claims, 18 Drawing Sheets

(56) References Cited

FOREIGN PATENT DOCUMENTS

| | | |
|---|---|---|
| EP | 1790301 A1 | 5/2007 |
| EP | 1925271 A1 | 5/2008 |
| WO | 9846173 A1 | 10/1998 |
| WO | 9912481 A1 | 3/1999 |
| WO | 9963913 A2 | 12/1999 |
| WO | 0023013 A1 | 4/2000 |
| WO | 0172246 A1 | 10/2001 |
| WO | 2006058018 A2 | 6/2006 |
| WO | 2007124352 A2 | 11/2007 |
| WO | 2009064787 A2 | 5/2009 |
| WO | 2010045231 A1 | 4/2010 |
| WO | 2010075555 A2 | 7/2010 |

OTHER PUBLICATIONS

Invitation to Pay Additional Fees and, Where Applicable, Protest Fee for PCT/PLC011/000013; dated Jun. 17, 2011; 6 pages.

PCT Notification of Transmittal of the International Search Report and Written Opinion of the International Searching Authority dated Aug. 17, 2011.

PCT Written Opinion of the International Searching Authority dated Aug. 17, 2011.

* cited by examiner

PROSTHESIS OF ANTERIOR SPINAL COLUMN, INSTRUMENT GUIDING THE PROSTHESIS AND METHOD FOR INSTALLATION THEREOF

RELATED APPLICATIONS

This non-provisional patent application claims priority benefit with regard to all common subject matter of the earlier filed Polish Patent Application titled "Prosthesis of anterior spinal column, instrument guiding the prosthesis and method for installation thereof", Polish Application Serial Number P390601, filed on Mar. 3, 2010, which is hereby incorporated by reference in its entirety into the present application.

BACKGROUND

1. Field

Embodiments of the present invention relate to prosthesis of an anterior spinal column, a prosthesis-guiding instrument and a method for installation thereof for use in the treatment of cervical, thoracic, and lumbar spinal segments.

2. Related Art

As described in U.S. patent application US2009/0149955, a spinal prosthesis is known in the form of a cylinder with a perforated wall and prostheses of intervertebral discs attached thereto made of spring silicone rubber in the shape of balloons. Anchoring of the cylinder in the damaged vertebra is provided by means of an entrapment of an elongate lug of the cylinder within a slot of a plate retained by screws within a recess of the damaged vertebra. Springs of resilient beads are attached to the natural vertebrae, superior and inferior to the damaged vertebra, by fixing plates provided with flanges that are fixed by screws to those vertebrae. Where adjoining vertebrae are damaged, two or more prosthetic cylinders for anchoring to a single vertebra are used with interconnecting resilient beads. The inconvenience of this solution is its complex structure and the necessity of boring into vertebral bone during installation of the prosthesis and fixing it with additional screws.

U.S. patent application US2006/064168 discloses a prosthesis for a partial replacement of a vertebral body, which has an upper contact plate for connection to an upper vertebral body, a lower contact plate for connection to a lower vertebral body, and a bridging part which connects the upper and lower contact plates to each other and bridges at least one vertebral body located between the upper and lower vertebral bodies. The bridging part is accommodated in a recess in the vertebral body. To be secured in said recess, the prosthesis has lateral anchoring projections, which penetrate into the bone substance, located on both sides of the bridging part. Its cross section narrows toward the rear preferably in a trapezoid shape. The inconvenience of this solution is the complex structure of the prosthesis and necessity of accommodating the bony recess to the bridging part to reinforce the support of the vertebral body.

A prosthesis for the replacement of all vertebral elements such as the vertebral body, the pedicles with the joint facets and the lamina, is disclosed in the European patent application EP1188424. This prosthesis has interconnection capability to a posterior fusion system by means of special screws. The prosthesis consists of a front part, which in a section is in an octagonal shape and screws that can connect the prosthesis to a posterior fixation pedicle screw system and thus create a complete construction which replaces a whole dislocated vertebral unit. The inconvenience of this solution is the necessity of cooperation with an additional posterior spinal stabilization by a posterior fusion system and the complicated two-stage surgical operation—first, using the posterior, and then using an anterior-lateral approach.

A prosthesis which has a telescopic perforated cylinder is disclosed in the European patent application EP 0968692 The cylinder consists of two parts and an intersected shield, connected by screws. The telescopic construction allows regulating the length of the prosthesis depending on the distance between the neighboring vertebrae. The prosthesis is situated in a definite position by two external screws fixed in the cylinder's hole. The cylinder is provided with teeth and other anchoring elements preventing sliding of the prosthesis and a decrease of its height during implantation. The inconvenience of this solution is the multi-element construction of the prosthesis. Bearing surfaces of the prosthesis are small, which decreases its load bearing capacity. The round shape of cylinders is not accommodated to the anatomy of the spine. For a proper placement of the prosthesis it is necessary to use an external element in the form of the above mentioned screws.

Another inconvenience of the solutions described above is the long duration of surgical implantation of the prosthesis between adjacent vertebrae, the necessity of its fastening with additional screws, and in some cases the necessity of additional stabilization, which complicates the surgery and prolongs implantation time.

A monorail system, which improves the use of the procedure of a spinal fusion, and a method for preparation of the intervertebral space and introduction of the implant are known from the patent application US 2007/0270873. The system consists of an instrument for distraction of the intervertebral space, preferably in the form of a rod having a rail, a chisel provided with a canal cooperating with the rail and an implant provided with a canal cooperating with the rail. The instrument for distraction, comprising a sliding section defined by the rail, cooperates with other instruments used for preparation of the intervertebral space and may act as an instrument for inserting the implant into the intervertebral space. The canals of the instrument and the implant are connected with the rail during guiding and controlling their insertion into the disc space. The inconvenience of this solution is a lack of the possibility of positioning and anchoring the instrument during insertion of the implant into the intervertebral space. Moreover, there is a possibility that the instrument may slide and harm sensitive tissues.

A method of installation of an expandable prosthesis for support of the anterior spinal column is known from instructions for an implant by LfC Sp. z.o.o. The method comprises resectioning vertebral body/bodies to enable secure, axial installation of a prosthesis and then measuring the resected space height. Next, this method comprises accurately selecting a prosthesis with regard to biomechanical and dimensional aspects corresponding to the size of the resected space, and filling the selected prosthesis with an autogenous bone graft or another material enabling bone fusion. Then this method includes inserting the prosthesis into surgically prepared space with a "spacer grasper" in a way enabling a free approach to a blocking screw, paying special attention to proper placement of external resistance rings with respect to a bearing surface of the vertebral body, so as not to irritate the spinal cord. The prosthesis is then extended with a "spacer dilator" to a required height, performing a desired distraction, and securing placement of the prosthesis between vertebral bodies, followed by complementing the inside of the prosthesis with an autogenous bone graft or anther material enabling bone fusion through special slots in sleeves. Next, the method may comprise screwing down the blocking screw into a transverse notch of an inner sleeve so as to stabilize and securely block the mutual position of both sleeves of the spacer, followed by releasing the instrument and withdrawing it from the surgical field.

A method of performance of vertebral body replacement surgery is known from instructions for the Expandable Corpectomy Device (ECD) implant of SYNTHES INC. The method comprises performing corpectomy and cleaning vertebral endplates, performing spinal segment distraction for setting the anatomic height of intervertebral space, selecting an implant size, and then connecting the implant to a holding-distraction instrument by placing the implant's teeth in notches of the implant. Next, this method comprises placing the prosthesis in a resected part of the spine and aligning it in a sagittal and frontal plane, the optimal arrangement of the implant being the center of the vertebral endplate. To provide bone fusion, some space around vertebral endplates has to be provided. Then the implant may be extended in situ with the holding-distraction instrument by rotating a handle of the instrument until a desired height of the implant is reached and the prosthesis anchors in vertebral endplates. The final steps of the method include releasing the implant from the instrument, and filling the space around the implant, especially its anterior part, with a bone graft or bone substitute.

The inconveniences of the above mentioned methods arise from their complexity and duration of surgery.

SUMMARY

The invention described herein relates to a prosthesis of an anterior spinal column, prosthesis-guiding instrument and method for installation thereof, which are applicable in the treatment of cervical, thoracic, and lumbar spinal segments.

Free of the inconveniences described above, the present invention comprises a prosthesis of elements of the anterior spinal column containing a perforated sleeve body provided with holes for bone overgrowth, hereinafter referred to as overgrowth holes, and at least one anchoring element on each of the end faces of the body. According to the invention, the body has in its wall at least one manipulative hole formed therethrough and at least one positioning hole cooperating with it. Longitudinal axes of both holes are parallel to each other. Depending on the embodiment, the positioning hole may also be formed through the body or formed only partially through the body (a "blind" hole) and made in the internal surface of the body from its internal side. The manipulative hole and positioning hole are elongated, circular, or of a shape comparable to a wheel.

Preferably, at least one end face and/or wall of the body are provided with at least one pair of opposite guidelines. A part of at least one end face of the body located at a side of the manipulative hole is inclined at an angle α not greater than 80° relative to the transverse axis of the body.

The wall of the body from its internal side is preferably provided with a bar, within which a gap is made. In one embodiment of the prosthesis, the wall of the body from its internal side is provided with a thread.

Inside the body, there is a positioner provided with overgrowth holes and at least one situating element cooperating with at least one of the positioning holes made in the body. The positioner is provided with at least one hole, situated within an inside diameter of the body's manipulative hole, cooperating with the known installation instrument. A length of the body's manipulative hole corresponds to a distance between extreme locations of the positioner's hole, which is situated within the inside diameter of the manipulative hole.

The positioner is in the form of a shaped solid, whose shape, depending on the embodiment, is comparable to a hollow barrel, a hollow cylinder, a bowl, or a polygon in at least a section thereof. Preferably, the positioner has a longitudinal cut constituting spring arms, which facilitate placement of the positioner inside the body.

The situating element in various embodiments is a pivot, a projection, a pin, a slot cooperating with an additional external fastening element, a hook, or a hump. The positioner's situating element in one embodiment is of a length approximate to the positioner's length.

In one embodiment, the positioner's wall from its external side is provided with a thread cooperating with another thread situated on the body's wall from its internal side.

Preferably, the positioner is provided with a projection cooperating with a gap made in a threshold of the body, securing the positioner against rotating within and falling out of the body.

In some embodiments, the hole in the positioner's wall is provided with a thread. For example, the positioner may be provided with an internal protrusion in which the positioner's hole is situated. The positioner's hole, depending on the embodiment, is a through hole or a blind hole. The through hole extends all the way through a wall of the positioner and the blind hole extends only partially through a wall of the positioner.

The prosthesis-guiding instrument of the present invention may be used for proper installation of the prosthesis of the anterior spinal column. Specifically, the prosthesis-guiding instrument may comprise a rod ended on one side with a holder and on the other side with a shaped working element provided with a sliding segment. According to various embodiments of the invention, the working element in the instrument has a guiding surface provided with at least one guide, a positioning surface situated on the opposite side of the working element, and a bearing surface situated with respect to the positioning surface at an angle β near or equal to 90°. The bearing surface may be provided with at least one anchoring element.

In some embodiments, the guiding surface and positioning surface of the working element are situated relative to each other at an angle γ not greater than 20°. The guiding surface of the working element may be convex or concave.

A part of the working element provided with the guiding surface in one embodiment is in a channel-like section, wherein both lateral walls are provided with at least one guide situated in parallel to the positioning surface of the guiding instrument.

The anchoring element of the guiding instrument may be fastened to the bearing surface in a separable or inseparable manner. In some embodiments, the anchoring element is in the form of a spike. Furthermore, the bearing surface may be provided with teeth.

According to various embodiments of the invention, a method of implantation of the prosthesis of the anterior spinal column in an intervertebral space may comprise the following steps. After resection of a vertebral body, in a surgically prepared intervertebral space, a distance between endplates of vertebrae adjacent to the resected vertebra is measured to select a prosthesis with a proper height, such that the height of the prosthesis together with anchoring elements is at least equal to the distance between vertebral endplates of adjacent vertebral bodies.

The prosthesis selected with regard to biomechanical and dimensional aspects may then be installed on an installation instrument through the positioner's hole situated in the inside diameter of the body's manipulative hole, therewith the prosthesis is filled with a material enabling bone fusion. In the method, according to various embodiments of the invention, the guiding instrument is situated in the intervertebral space by resting its working element's bearing surface against the external surface of the vertebral body and placing the guiding instrument's anchoring element into this vertebral body to secure the proper location of the instrument and to restrict its mobility with respect to the vertebral body.

Next, the installation instrument with the prosthesis installed on it is placed into the intervertebral space, resting the anchoring elements situated on the prosthesis end face unilaterally against the vertebral endplate opposite the vertebra, on which the guiding instrument is situated. Then, with a rotational motion of the guiding instrument, the prosthesis is placed deep inside the intervertebral space along at least one guide of the guiding instrument cooperating with at least one pair of opposite guidelines made in the prosthesis body. Simultaneously, distraction of the resected space is performed using the guiding instrument. A support and rotation point is located on the anchoring elements situated on the body's end face embedded in the vertebral body. Upon proper location of the prosthesis in the intervertebral space, the prosthesis is held in position by the installation instrument, and the guiding instrument is pulled out of the intervertebral space. Next, the installation instrument is disconnected from the prosthesis. In one embodiment of the method of implantation, after placing the prosthesis in the intervertebral space, the prosthesis may be additionally supported and fixed with an external stabilizer using fastening means screwed in the positioner's hole situated in the manipulative hole of the body.

The present invention may increase precision of implantation, decrease the level of complexity of surgery, shorten the duration of surgery and improve its safety. The construction of the prosthesis allows for independent support of the anterior spinal column without the necessity of using additional stabilization, due to the prosthesis shape comparable to the shape of a vertebral body and because the prosthesis is made of a material with properties comparable to bone properties. The application of the internal positioner assures an attachment of the installation instrument during implantation through the positioner's hole located in the inside diameter of the body's manipulative hole. The prosthesis can also be connected with an additional stabilizer using a screw screwed in the positioner's hole situated in the inside diameter of the body's manipulative hole. Because the positioner is not in contact with the vertebral bones, it does not transfer the loads acting on the prosthesis. For the installation of the prosthesis, it is sufficient to use only two instruments: the installation instrument and the guiding instrument, which assure distraction of the intervertebral space and precise placement of the prosthesis within the space. The construction of the guiding instrument assures accurate and secure introduction of the prosthesis into the intervertebral space.

Service simplicity and ease of applying the instrumentation assure high precision and quickness of implantation, as well as an improvement in patient safety. A wide range of prosthesis' dimensions enables their application in most patients, assuring high ergonomics of surgeon's work.

BRIEF DESCRIPTION OF THE DRAWING FIGURES

Embodiments of the present invention are described in detail below with reference to the attached drawing figures, wherein.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
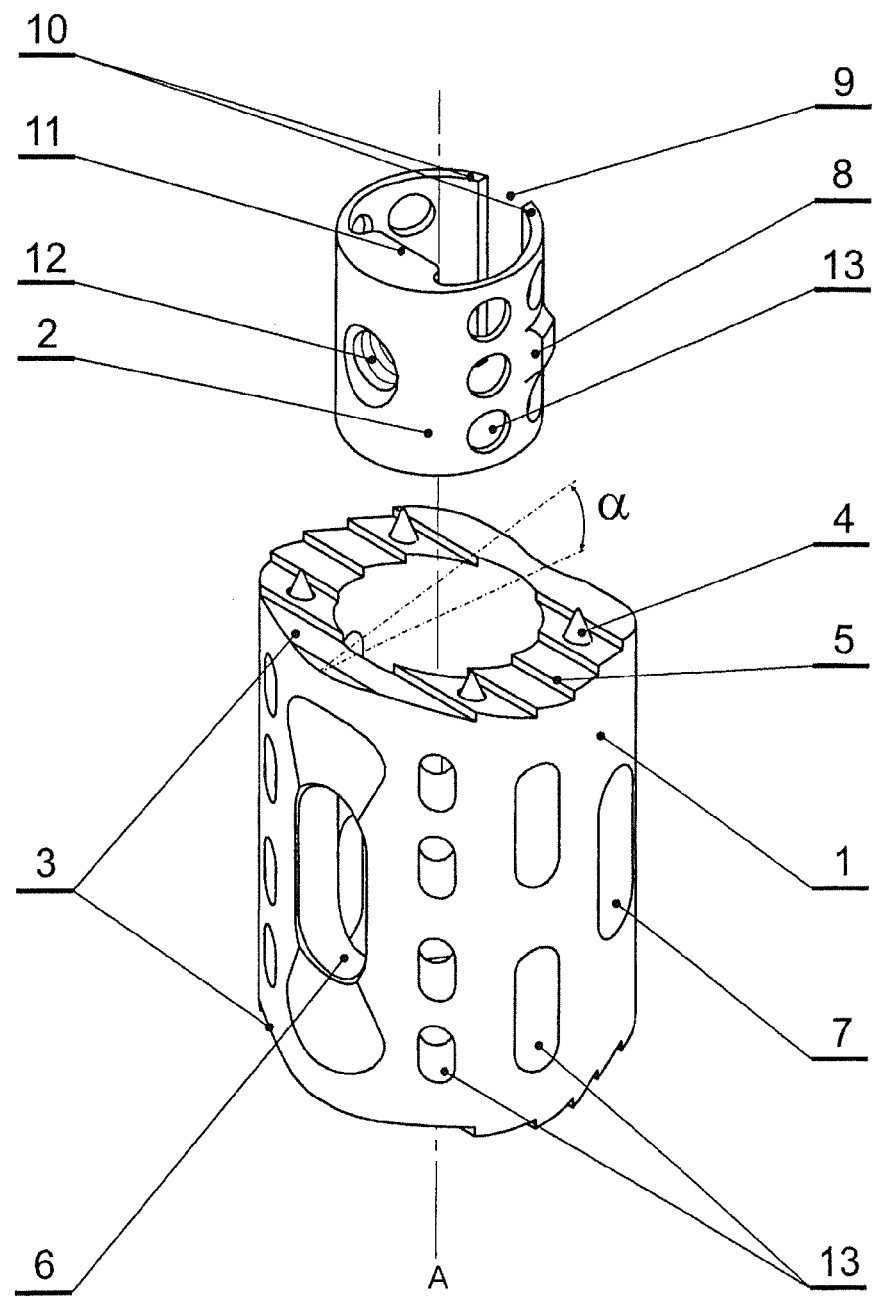
FIG. 1 is an exploded perspective view illustrating a body and a positioner constructed in accordance with embodiments of the present invention.

FIG. 1 illustrates a prosthesis of an anterior spinal column, the prosthesis comprising a body 1 in the form of a perforated sleeve, and a positioner 2 cooperating with the body 1 and situated therein. In various embodiments of the invention, the body 1 is a hollow, cylindrical component comprising, on every end face 3, four anchoring elements 4 in the form of spikes and teeth 5. An elongated manipulative hole 6 configured to correspond with an anterior site of a spine may be formed through a wall of the body 1. An elongated positioning hole 7 may also be formed through the wall of the body 1 and may be spaced apart circumferentially from the manipulative hole 6. A longitudinal axis of the positioning hole 7 may be parallel to a longitudinal axis of the manipulative hole 6. Longitudinal axes of the manipulative holes 6 and positioning hole 7 may be parallel to a longitudinal center axis A of the body 1. Each end face 3 may be cut from a side of the body 1 where the manipulative hole 6 is located and deflected from a transverse axis (i.e., perpendicular to center axis A) of body 1 at an angle α, which may be greater than 0° and less than 90°. For example, the angle α may be approximately 42°, which may render it possible in an initial phase of installation to embed and anchor the spikes 4 in upper and lower vertebral endplates. The end face 3 of the body 1 may be inclined at an angle enabling the introduction of the prosthesis and fitting it to a patient's spine anatomy.

The positioner 2 may be a hollowed cylindrical component. On an external surface of the positioner 2, there may be a situating element 8 in the form of a pivot situated in the positioning hole 7 of the body 1, limiting mobility of the positioner 2 inside the body 1. A pivot, as used herein, may be a protrusion, as illustrated in FIG. 1. The positioner 2 may have a longitudinal cut 9 therethrough forming spring arms 10 and enabling their deflection for a more efficient introduction of the positioner 2 into the inside of the body 1. The positioner 2 may also comprise an internal protrusion 11, through which a threaded through hole 12 is formed. The internal protrusion 11 may be an inner thickened area. In some embodiments of the invention, as later described herein, the hole 12 may alternatively not be threaded. The through hole 12 may be aligned with and positioned radially inward of the body's 1 manipulative hole 6. The hole 12 enables attachment of an end of an installation instrument, as later described herein, and this in turn improves the process of installing the prosthesis in an intervertebral space. In order to accelerate overgrowth of the prosthesis with bone tissue, both the wall of the body 1 and the positioner 2 are provided with overgrowth holes 13.

Figure 2:
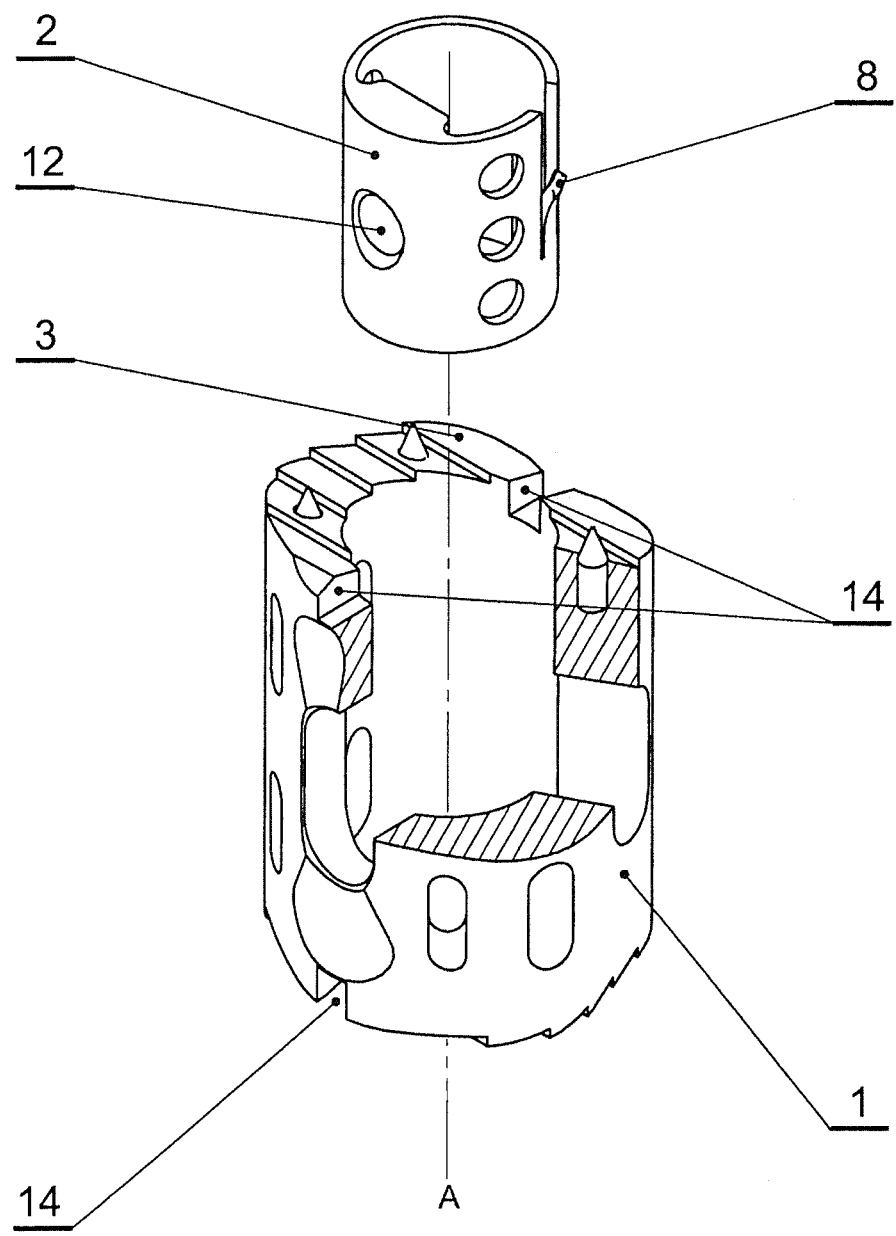
FIG. 2 is an exploded, sectional perspective view of the body and positioner of FIG. 1.

In one embodiment of the invention presented in FIG. 2, each end face 3 of the body 1 is provided with a pair of opposite guidelines 14 which may cooperate with a guide of a guiding instrument, as later described herein. In this embodiment of the invention, the positioner 2 is in the form of a hollowed, longitudinally cut cylinder provided with the situating element 8 in the form of a hook on a strip formed between the cuts. The hole 12 of the positioner 2 is non-threaded in this alternative embodiment of the invention illustrated in FIG. 2.

Figure 3:
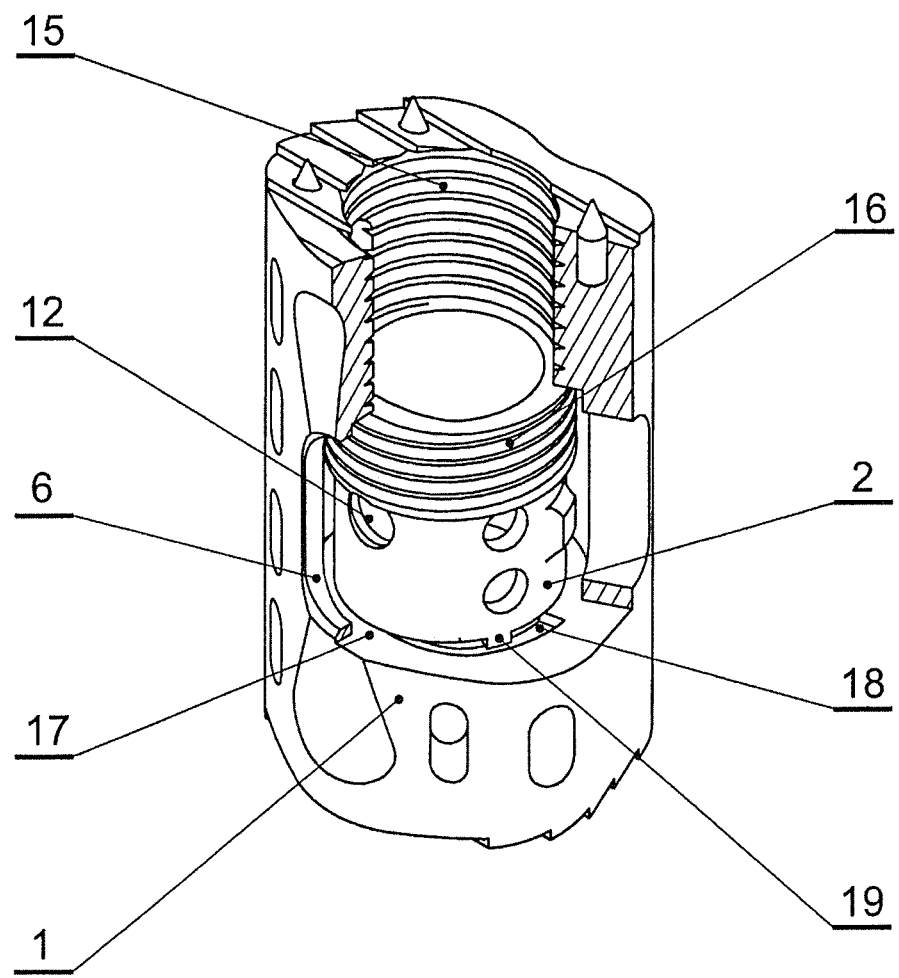
FIG. 3 is a sectional perspective view of the body and the positioner situated within the body, the positioner being in the form of a hollowed cylinder provided with a thread on a part of its external surface.

In another embodiment of the invention presented in FIG. 3, a wall of the body 1 from its internal side is provided in a part of its length with a thread 15, whereas the positioner 2 situated inside the body 1 is provided on a part of its wall from its external side with a thread 16 cooperating with the thread 15 on the body's 1 wall from its internal side. To prevent the positioner 2 from falling out of the body 1, the wall of the body 1 from its internal side is provided with a threshold 17, within which a gap 18 is made. The gap 18 may cooperate with a projection 19 made on the wall of positioner 2 from its external side. The gap 18 prevents the positioner 2 from rotating inside the body 1 and facilitates positioning the hole 12 of the positioner 2 radially inward from the manipulative hole 6 or within the inside diameter of the manipulative hole 6 of body 1.

Figure 4:
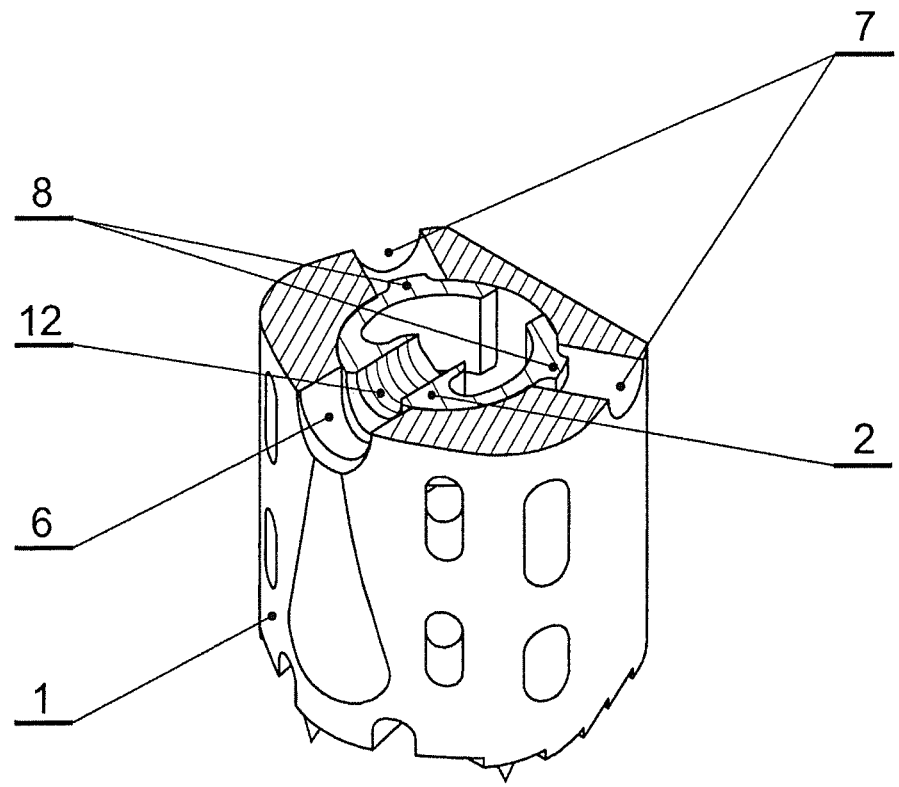
FIG. 4 is a cross-sectional perspective view presenting in a transverse section the body with the positioner situated within it, the positioner being in a configuration of a hollowed cylinder provided with two situating elements in the form of pivots.

In another embodiment of the invention presented in FIG. 4, the body 1 has formed through its wall two positioning holes 7 located on both sides of the manipulative hole 6. Manipulative hole 6 and positioning holes 7 are in a shape similar to a wheel. In this embodiment of the invention, the positioner 2 is provided with two situating elements 8 in the form of pivots located on both sides of the hole 12 and situated in positioning holes 7 of the body 1.

Figure 5:
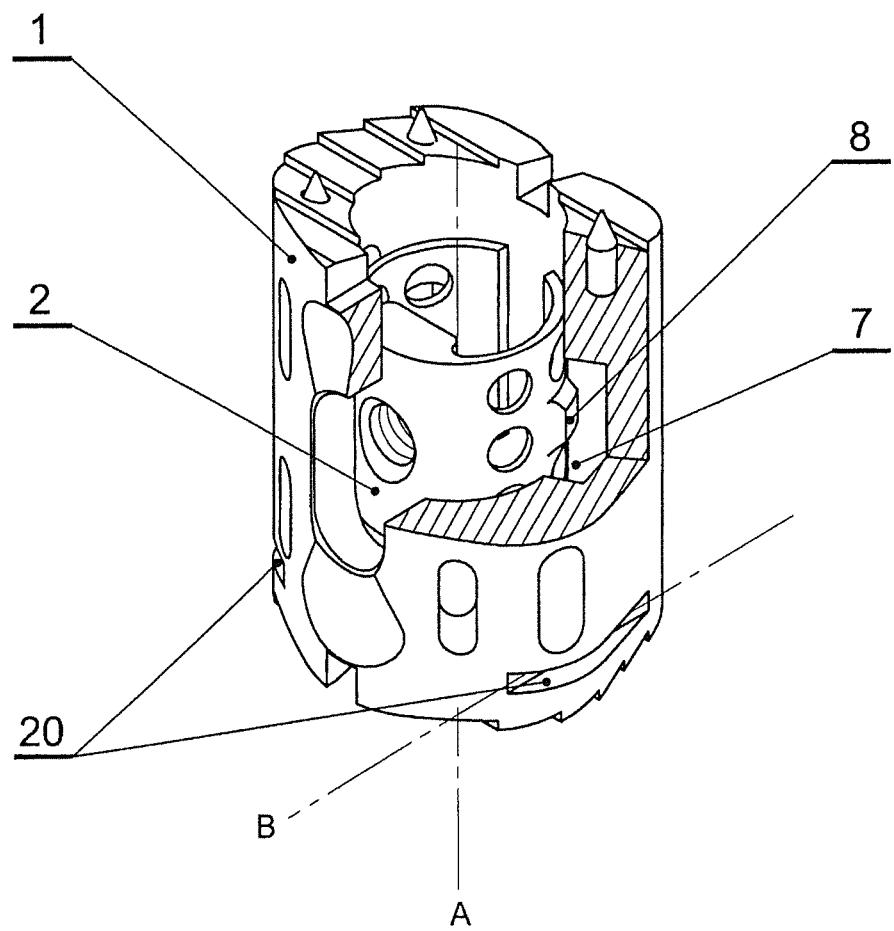
FIG. 5 is a sectional perspective view of the body, provided with a blind positioning hole and the positioner situated within the body in the configuration of a hollowed cylinder.

In still another embodiment of the invention presented in FIG. 5, the positioner's 2 situating element 8, in the form of a pivot, is situated in the elongated positioning hole 7. In this embodiment of the invention, the elongated positioning hole 7 is formed as a blind hole or cavity extending only partially through the body's 1 wall from its internal side. In the wall of the body 1, a pair of opposite guidelines 20 or channels is made with a longitudinal axes B lying in a plane perpendicular to the longitudinal axis A of the body 1, as illustrated in FIG. 5.

Figure 6:
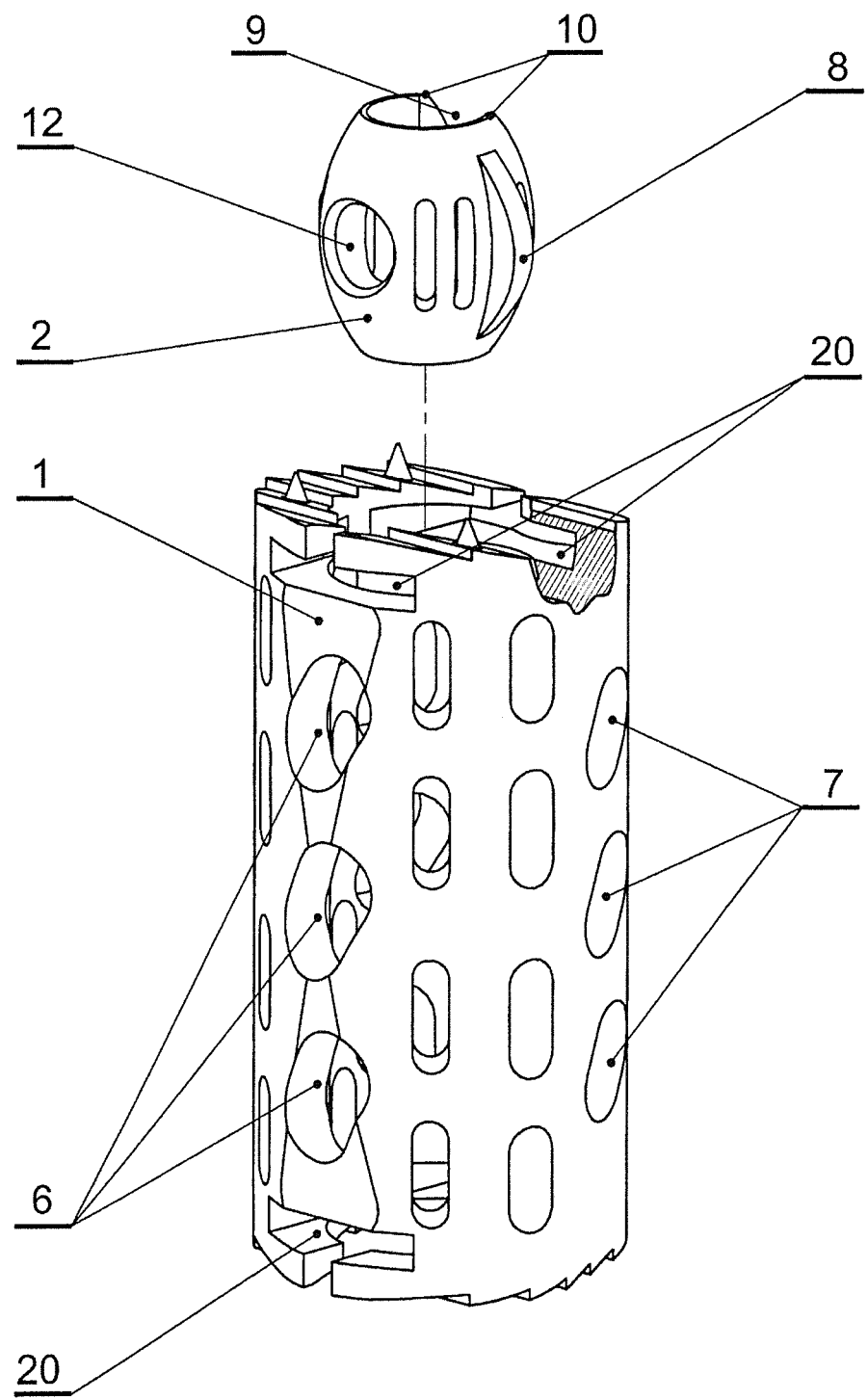
FIG. 6 is an exploded perspective view of the body provided with three elongated oblique manipulative holes and three elongated oblique positioning holes and the positioner in a configuration similar to a hollowed barrel.

In another embodiment of the invention presented in FIG. 6, the body 1 has three elongated oblique manipulative holes 6 and three elongated oblique positioning holes 7 formed through its wall. The wall of body 1 is provided with a pair of opposite channels or guidelines 20 in a shape similar to the letter T. The positioner 2 is shaped similar to a hollowed barrel and is provided with the longitudinal cut 9 forming the spring arms 10. The hole 12 of the positioner 2 in this embodiment of the invention is not threaded. The positioner 2 is equipped with the situating element 8 in the form of a projection with a length corresponding approximately with the positioner's 2 length. The situating element 8 is located on the positioner's wall from its external side.

Figure 7:
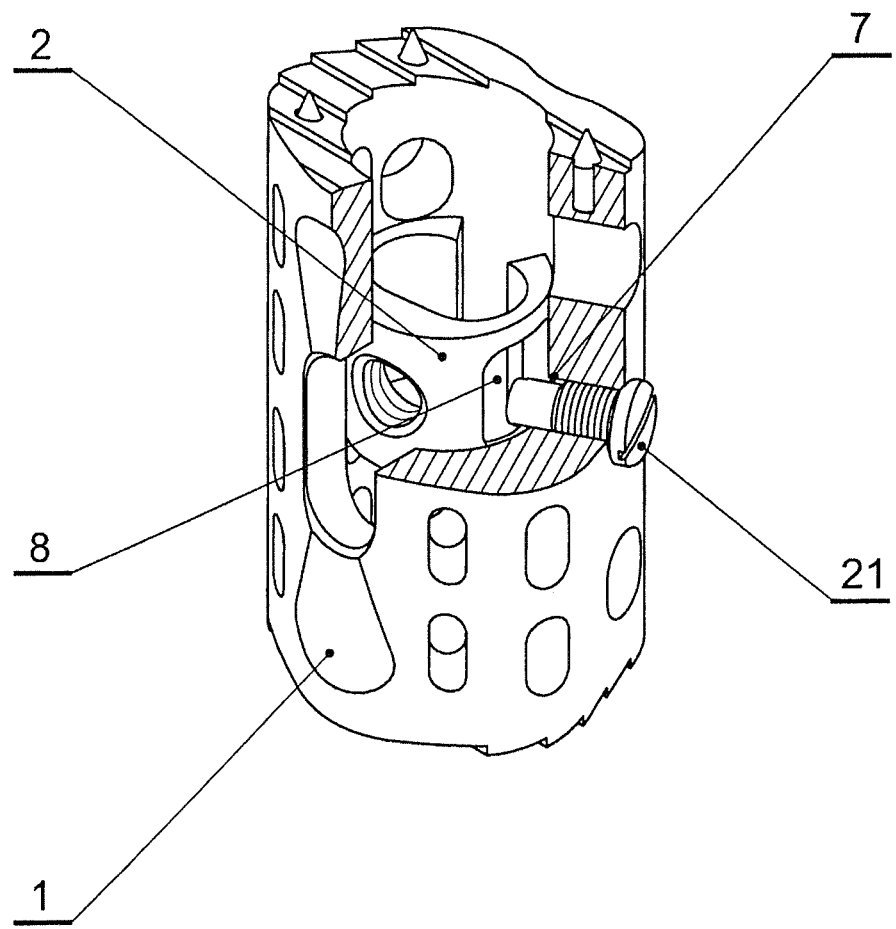
FIG. 7 is a sectional perspective view of the body and the positioner situated within the body, having the configuration of a hollowed cylinder, with the situating element in the form of a slot.

In another embodiment of the invention presented in FIG. 7, the situating element 8 of the positioner 2 has an elongated slot formed therethrough for an additional fixing element 21 in the form of a screw situated in the positioning hole 7 of the body 1.

Figure 8:
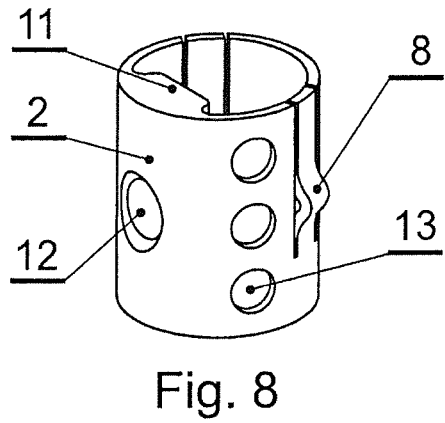
FIG. 8 is a perspective view of the positioner in the form of a hollowed cylinder provided with a hump.

FIGS. 8-12 present further embodiments of the positioner 2. The positioner 2 presented in FIG. 8 is in the form of a hollow, longitudinally cut cylinder provided with the situating element 8 in the form of a hump on a strip of the positioner's wall formed between two longitudinal cuts. The positioner 2 is provided with the internal protrusion 11, also referenced herein as an inner thickened area 11, wherein a non-threaded through hole 12 is made.

Figure 9:
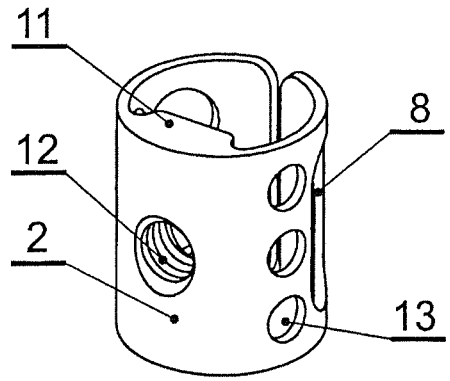
FIG. 9 is a perspective view of the positioner in the form of a hollowed cylinder with the situating element in the form of a slot.

The positioner 2 shown in FIG. 9 is in the form of a hollowed cylinder. The situating element 8 of the positioner 2 is an elongated slot formed through the wall of the positioner 2. The positioner 2 is provided with the internal protrusion 11, wherein the threaded through hole 12 is made.

Figure 10:
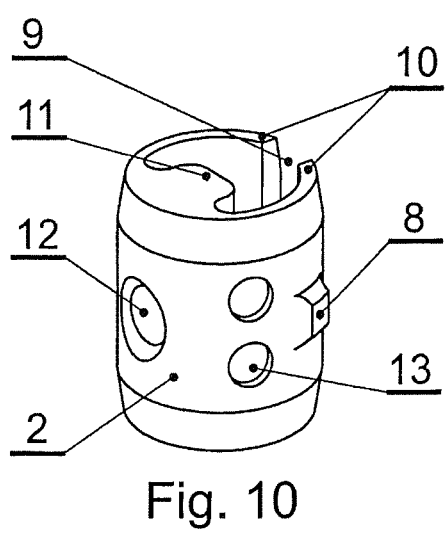
FIG. 10 is a perspective view of the positioner in a form similar to a hollowed barrel.

The positioner 2 presented in FIG. 10 is in the form similar to a hollowed barrel. On its wall from the external side is located the situating element 8 in the form of a pivot. The positioner 2 is provided with the longitudinal cut 9 forming the spring arms 10. The positioner 2 is provided with the internal protrusion 11, wherein the threaded through hole 12 is made.

Figure 11:
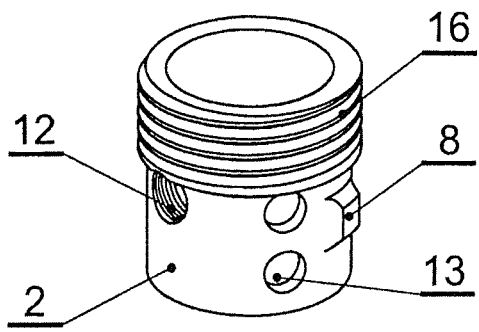
FIG. 11 is a perspective view of the positioner in the form of a hollowed cylinder, provided with a thread on a part of the wall from its external surface.

The positioner 2 shown in FIG. 11 is in the form of a hollowed cylinder provided with the thread 16 in a part of the wall from its external side. The positioner 2 has the threaded hole 12 formed therethrough, and the situating element 8 in the form of a pivot is located on its wall from the external side.

Figure 12:
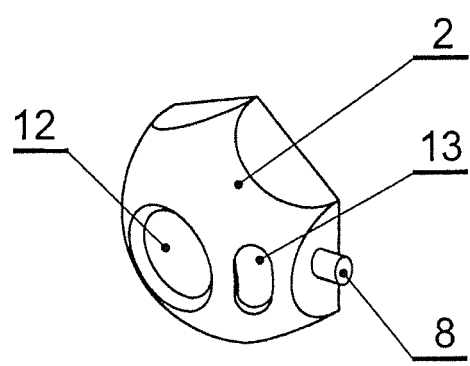
FIG. 12 is a perspective view of the positioner in a form similar to a bowl having a transverse section of a polygon.

In an embodiment presented in FIG. 12, the positioner 2 is in the form similar to a hollowed bowl ended with planes forming a polygon in a transverse section. The positioner 2 is provided with the non-threaded embodiment of the hole 12 and the situating element 8 is in the form of a pin situated on the positioner's 2 wall from its external side. For acceleration of prosthesis overgrowth with bone tissue, all embodiments of the positioner 2 may be provided with overgrowth holes 13, as illustrated in FIGS. 8-12.

Figure 13:
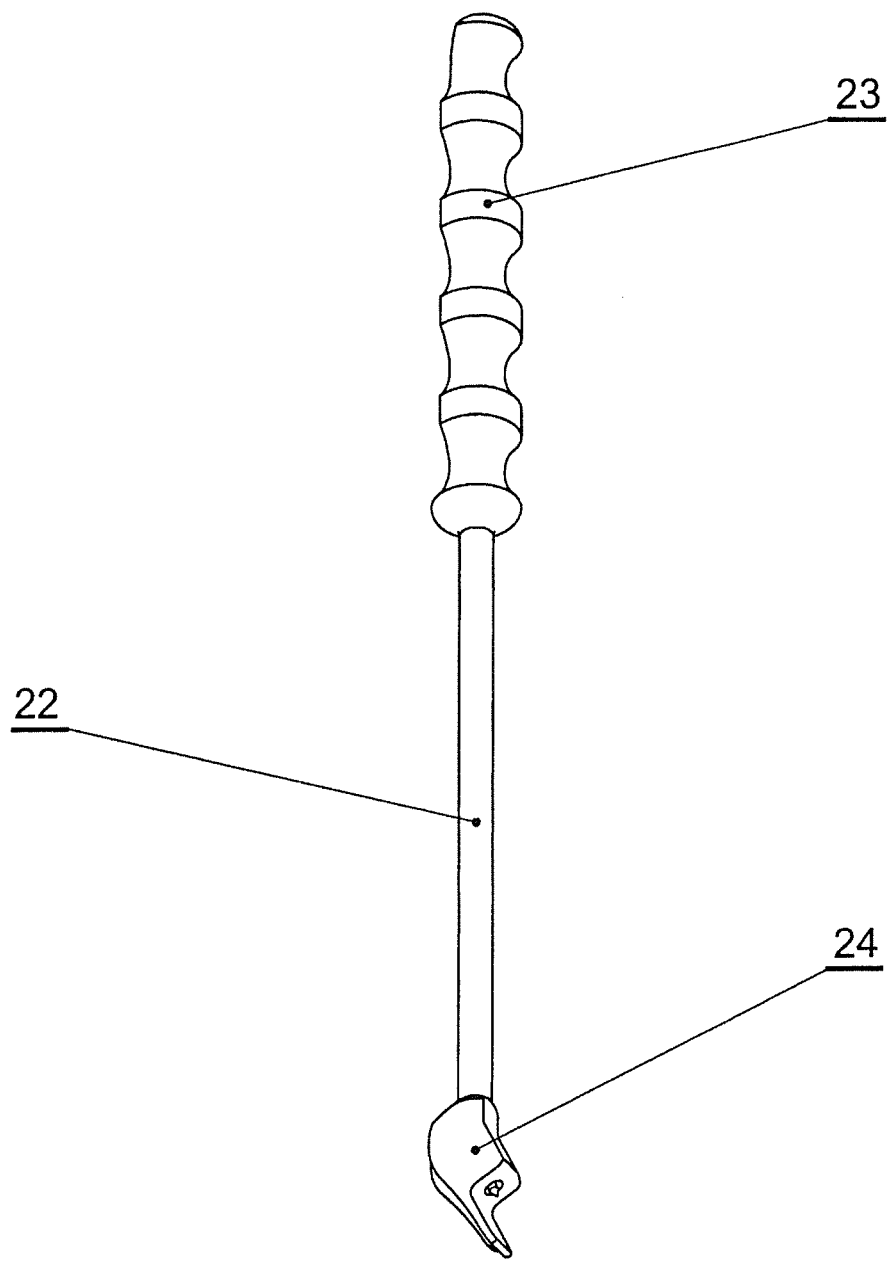
FIG. 13 is a perspective view of a guiding instrument constructed in accordance with embodiments of the present invention.

The guiding instrument presented in FIG. 13 is in the form of a rod 22 ended with a handle 23 on one of its ends, and a working element 24 on its other end.

Figure 14:
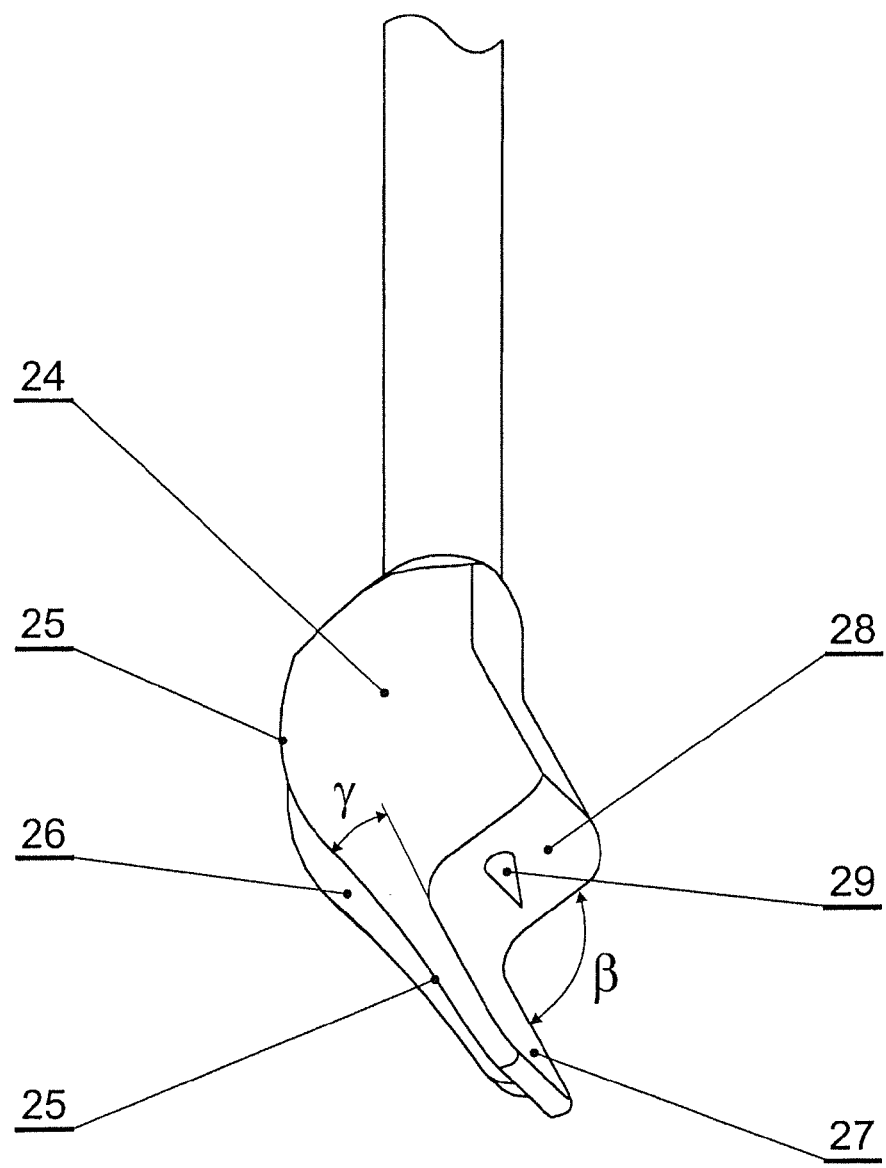
FIG. 14 is a fragmentary perspective view of the guiding instrument of FIG. 13, illustrating a working element of the guiding instrument.

The working element 24 of the guiding instrument presented in FIG. 14 may comprise a guiding surface 25 which may be convex. The guiding surface 25 may be provided with a shaped guide 26 configured for cooperating with the guidelines 14, such as those illustrated in FIG. 2, located in the end face 3 of the body 1. The working element 24 of the guiding instrument has a positioning surface 27 and a bearing surface 28 situated relative to the positioning surface 27 at an angle 3, which may be equal to approximately 90°; the bearing surface 28 fixes the guiding instrument in a proper position relative to the vertebral body. The guiding surface 25 and positioning surface 27 of the working element 24 may be situated relative to each other at an angle γ, which may be equal to approximately 10° forming a wedge. On the bearing surface 28 there may be an anchoring element 29 in the form of an immobile spike, enabling anchoring of the guiding instrument in a bone of the vertebral body. The positioning surface 27 and bearing surface 28 are situated on the other side of the guiding surface 25.

Figure 15:
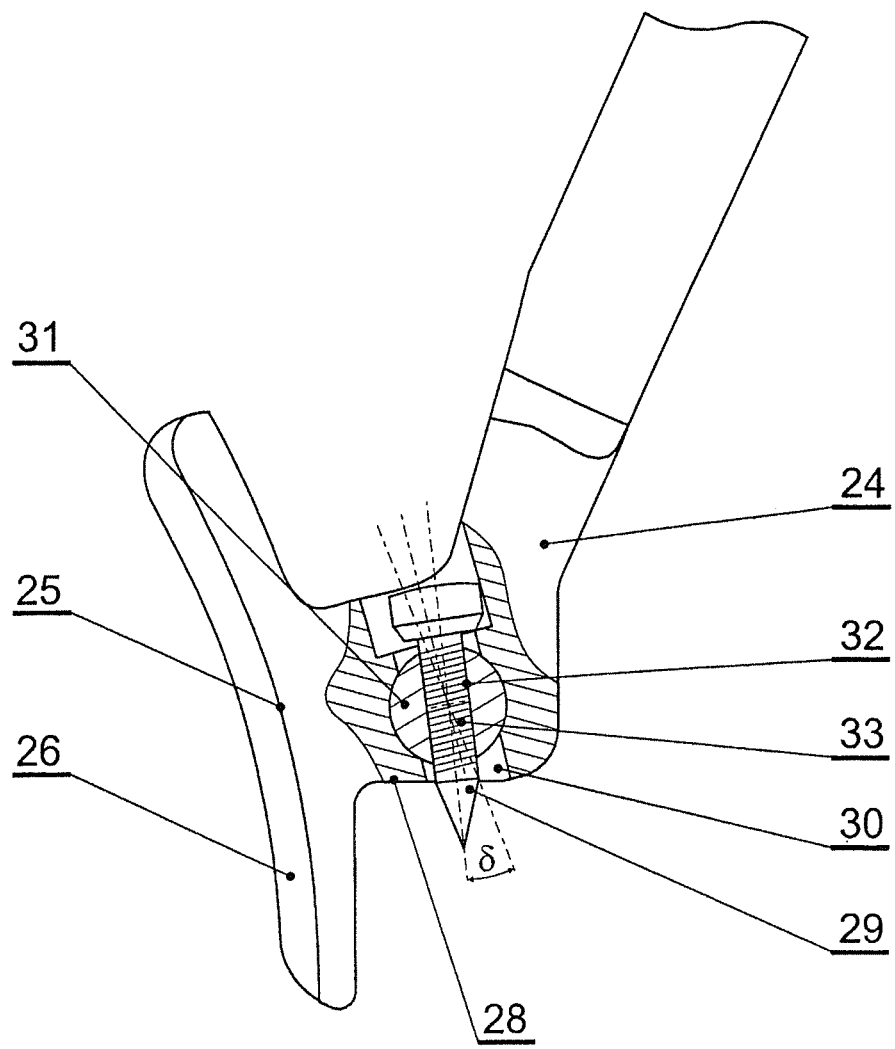
FIG. 15 is a fragmentary, cutaway side view of the working element of the guiding instrument of FIG. 13 provided with a movable anchoring element in the form of a spike.

In an embodiment of the invention presented in FIG. 15, the guiding surface 25 of the working element 24 may be concave and provided with the shaped guide 26. The bearing surface 28 of the working element 24 is provided with the anchoring element 29 in the form of a movable spike. Within the working element 24 of the guiding instrument, in a plane approximately perpendicular to the bearing surface 28, an elongated port 30 is made, in which a rotationally movable cylinder 31 is located. The movable cylinder 31 has a threaded port 32 in its lateral wall. The port 32 enables screwing the anchoring element 29 into the cylinder 31. The anchoring element 29 is in the form of a spike and is provided with a thread 33 on the part located within the working element 24. It allows regulation of the sliding out of the anchoring element 29 from above the bearing surface 28 of the working element 24. The anchoring element 29 in the form of a spike may move in a swinging way within the inside diameter of the elongated port 30 due to rotational movement of the cylinder 31 in a range of angle δ, which may be, for example, ±4°. This movement takes place only in one plane.

Figure 16:
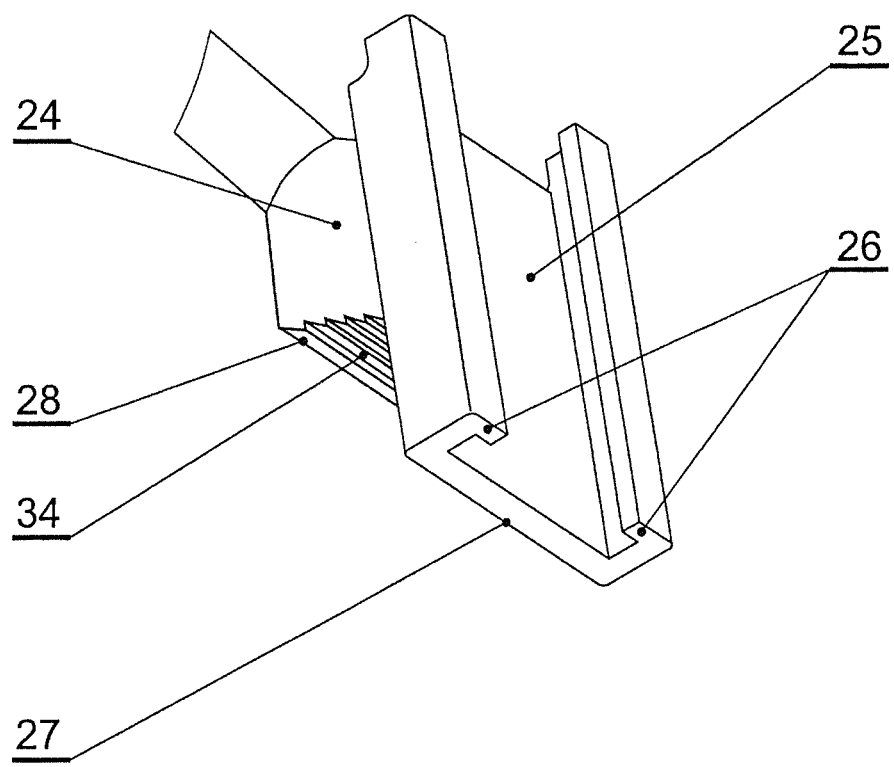
FIG. 16 is a perspective view of the working element of the guiding instrument, having a guiding surface in a shape comparable to a channel.

In an embodiment of the invention shown in FIG. 16, a part of the working element 24 provided with the guiding surface 25 is in a form comparable to a channel. The guides 26 are situated on edges of both walls in parallel to the positioning surface 27. The bearing surface 28 is provided with teeth 34 preventing the bearing surface 28 from uncontrolled movement along the vertebral body.

Figure 17:
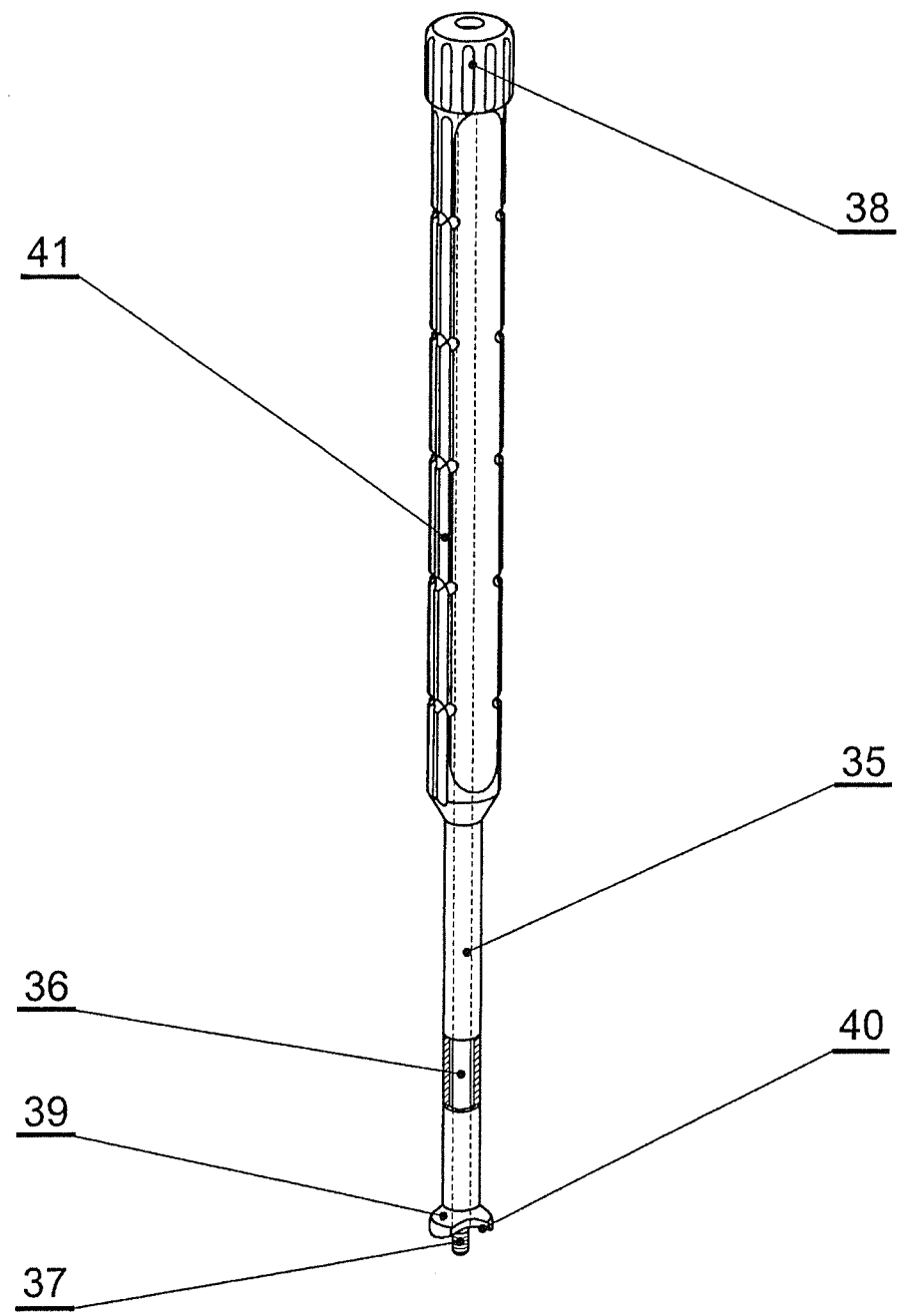
FIG. 17 is a perspective view of an installation instrument constructed in accordance with embodiments of the present invention.

The installation instrument presented in FIG. 17 comprises a sleeve 35, within which a tang 36 is located. One end of the tang 36 may comprise a junction 37 enabling provisional connection with the hole 12 in the positioner 2, illustrated in FIGS. 1-12. An opposing end of the tang 36 may comprise a knob 38 cooperating with a substantially identical junction (not shown). The end of the sleeve 35 proximate the junction 37 is provided with a collar 39 with a bearing plane 40. The bearing plane 40 of the collar 39 has a profile similar to the shape of the prosthesis body's 1 profile, which allows precise adjustment of the instrument to the body 1 of the prosthesis and prevents the body 1 from moving relative to the installation instrument, thus improving precision of prosthesis installation. A holder 41 may be mounted on the sleeve 35 underneath the knob 38.

Figure 18:
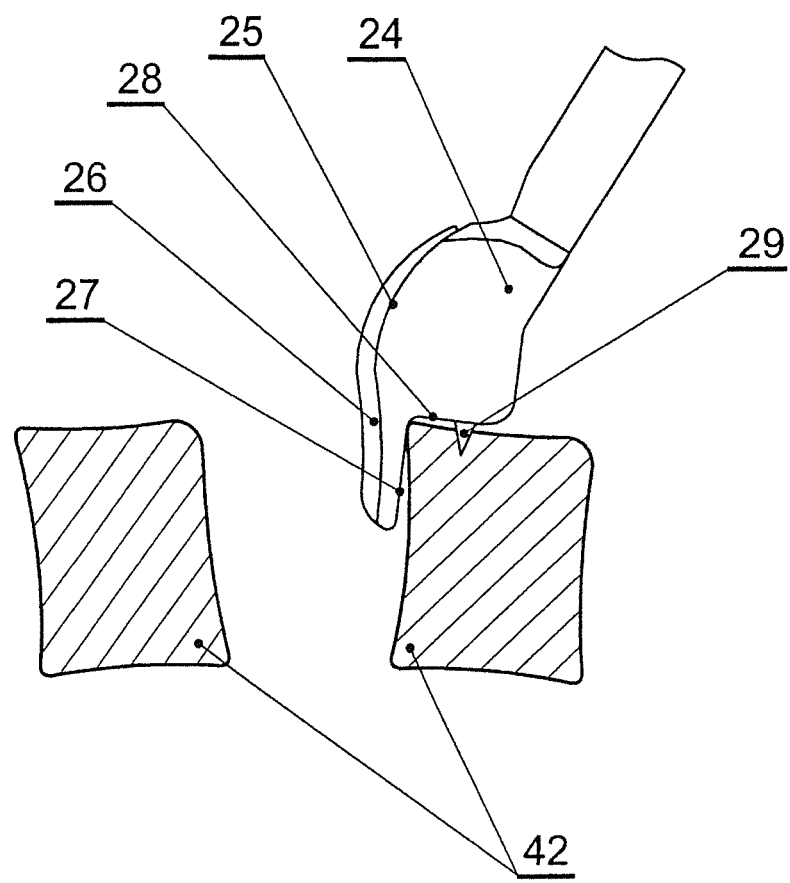
FIG. 18 is a fragmentary side view of the guiding instrument with a convex guiding surface introduced into an intervertebral space.

FIG. 18 illustrates the guiding instrument of FIGS. 13 and 14 introduced into an intervertebral space. The working element 24 of the guiding instrument has the convex guiding surface 25, provided with the shaped guide 26, the positioning surface 27, and the bearing surface 28 situated relative to the positioning surface 27 at an angle β, which may be equal to approximately 90°. The positioning surface 27 and bearing surface 28 are situated on an opposite side of the working element 24 relative to the guiding surface 25. On the bearing surface 28 is located the anchoring element 29 in the form of the immobile spike. The bearing surface 28 of the guiding instrument is rested against the external part of the vertebral body 42, within which the anchoring element 29 is situated.

Figure 19:
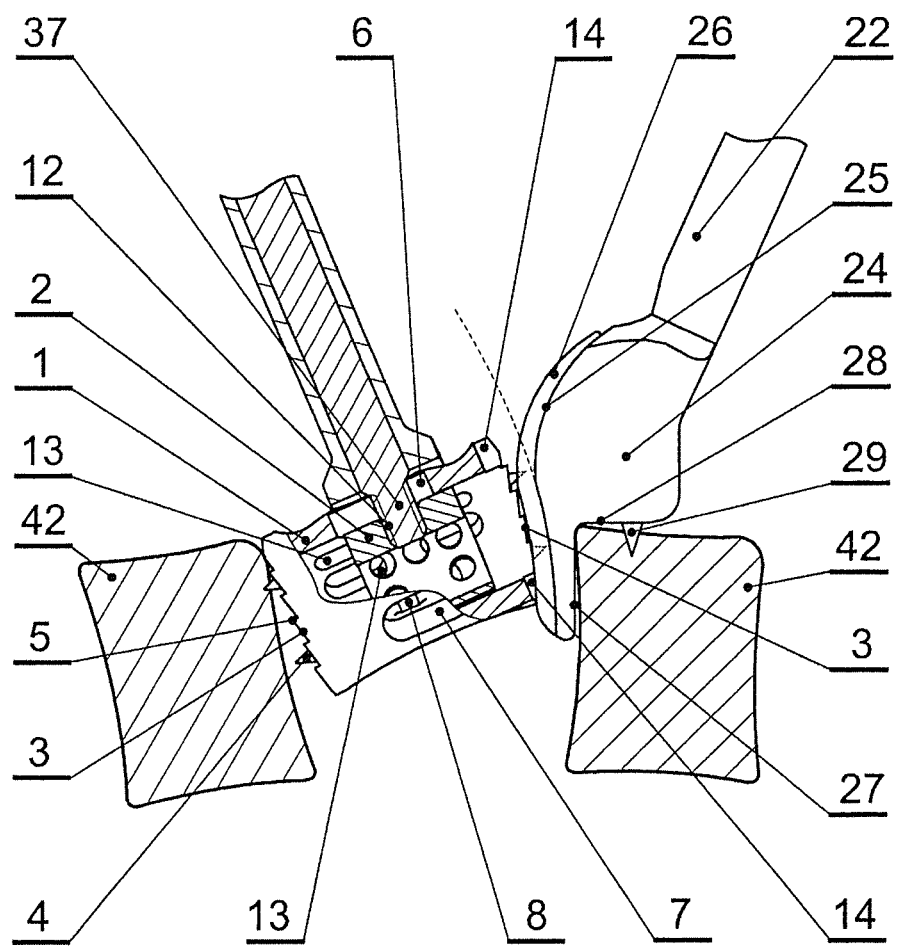
FIG. 19 is a fragmentary side view of the guiding instrument and a cutaway side view of the installation instrument, illustrating a method step of prosthesis installation within the intervertebral space.

A method of installation of the prosthesis of the anterior spinal column is illustrated in FIG. 19. After resection of the vertebral body, in thus surgically prepared intervertebral space, a distance between endplates of vertebral bodies 42 adjacent to the resected vertebra is measured to select a prosthesis with a proper height, providing that the height of the prosthesis together with anchoring elements 4 is at least equal to the distance between endplates of adjacent vertebral bodies 42. The prosthesis, selected with regard to biomechanical and dimensional aspects, for installation in the intervertebral space consists of the sleeve body 1 whose each end face 3 is provided with the four anchoring elements 4 in the form of spikes, the teeth 5 and the pair of opposite guidelines 14; the sleeve body 1 has in its wall the elongated manipulative hole 6, and the elongated positioning hole 7 and the positioner 2, situated inside the body 1, in the shape of a hollowed cylinder provided with the hole 12 in its threaded configuration, situated within the inside diameter of the body's 1 manipulative hole 6 and the situating element 8 in the form of a pivot located in the positioning hole 7 of the body 1, and also the longitudinal cut 9, which forms spring arms 10, as illustrated in FIGS. 1-12.

As further illustrated in FIG. 13, both the body 1 and positioner 2 are provided with overgrowth holes 13 for filling the prosthesis with a material enabling bone overgrowth. The prosthesis that has been selected is installed on the junction 37 of the installation instrument through the positioner's 2 threaded hole 12 situated in the body's 1 elongated manipulative hole 6. Next, the prosthesis is filled with a material enabling bone fusion, using a mallet of bony fragments. Then the guiding instrument is situated in the intervertebral space. The guiding instrument is in the form of the rod 22 ended with the handle 23 on the one side, as illustrated in FIG. 13, and the working element 24 on the other side. The working element 24 of the guiding instrument has the convex guiding surface 25, provided with the shaped guide 26, cooperating with the pair of opposite guidelines 14 located in the end face 3 of the body 1. The working element 24 of the guiding instrument has the positioning surface 27 and the bearing surface 28 situated relative to the positioning surface 27 at an angle β, which may be equal to approximately 90°. The bearing surface 28 fixes the guiding instrument in a proper position with respect to the vertebral body. On the bearing surface 28 is located the anchoring element 29 in the form of an immobile spike. The positioning surface 27 and the bearing surface 28 are situated on an opposite side of the working element 24 than the guiding surface 25.

The guiding instrument is introduced to the intervertebral space by resting its bearing surface 28 against the external part of the vertebral body 42 and the guiding instrument's immobile anchoring element 29 is placed in this vertebral body in order to place the guiding instrument properly and restrict its mobility relative to the vertebral body 42. Next, the installation instrument with the prosthesis installed on it is placed in the intervertebral space by unilaterally resting the anchoring elements 4 against the endplate of a vertebra 42 opposite the vertebra 42 on which the guiding instrument is placed. Next, with rotational movement of the guiding instrument the prosthesis is positioned deep inside the intervertebral space along the guide 26 of the guiding instrument cooperating with the pair of opposite guidelines 14 of the prosthesis body 1. The intervertebral space is simultaneously distracted with the use of the guiding instrument, where the support and rotation point is located on the anchoring elements 4 in the form of spikes situated on the end face 3 of body 1 embedded in the endplate of the vertebral body 42. After placement, the prosthesis is held in position by means of the installation instrument and the guiding instrument, as illustrated in any of FIGS. 14-16, is removed from the intervertebral space. Next, the installation instrument, as illustrated in FIG. 17, is disconnected from the prosthesis body 1.

Figure 20:
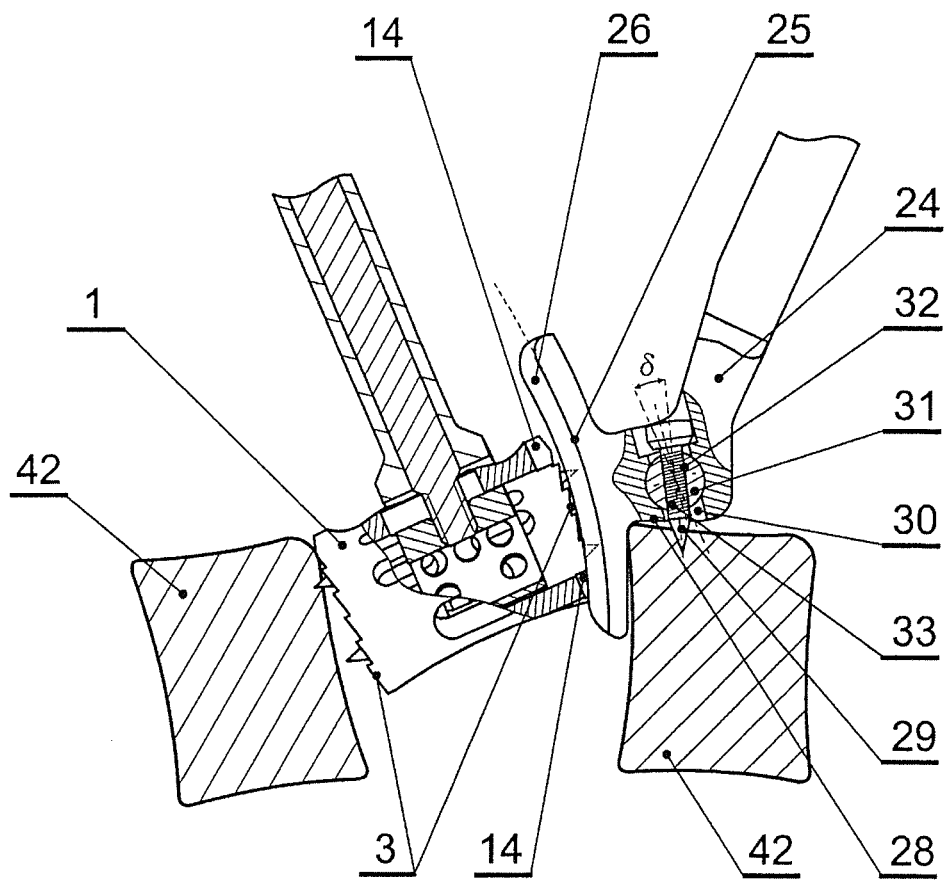
FIG. 20 is a fragmentary, cutaway side view of the guiding instrument and the installation instrument, illustrating another method step of prosthesis installation wherein the guiding instrument includes a movable anchoring element in the form of a spike.

FIG. 20 shows an example of installation of the prosthesis with the use of the guiding instrument, whose working element 24 has the concave guiding surface 25 provided with the shaped guide 26 cooperating with the pair of opposite guidelines 14 in the end face 3 of body 1. The movable anchoring element 29 in the form of the movable spike is located on the bearing surface 28 of the guiding instrument. Within the working element 24 of the guiding instrument, in a plane approximately perpendicular to the guiding surface 28 there is the elongated port 30, within which the rotationally movable cylinder 31 is located, having in its lateral wall the threaded port 32, as described above in reference to FIG. 15. The port 32 enables screwing the anchoring element 29 into the cylinder 31. The anchoring element 29 is provided with the thread 33 on the part located within the working element 24. It allows the regulation of jut of the anchoring element 29 from above the bearing surface 28 of the working element 24. The anchoring element 29 may move in a swinging way within the inside diameter of the elongated through port 30 due to rotational movement of the cylinder 31 in a range of angle δ changes of approximately ±4°. This movement takes place only in one plane.

In FIG. 20, the guiding instrument is introduced to the intervertebral space by resting its bearing surface 28 against the external part of the vertebral body 42 and the movable anchoring element 29 is placed into this vertebral body 42. Next, the installation instrument with the prosthesis installed on it is positioned in the intervertebral space by unilaterally resting the anchoring elements 4 of the body 1 against the endplate of the vertebra 42 opposite the vertebra 42 on which the guiding instrument is placed. Next, the guiding surface 25 of the working element 24 of the guiding instrument is deflected from the vertebral body 42 and the placement of the prosthesis into the intervertebral space starts along the guide 26 of the guiding instrument, cooperating with the pair of opposite guidelines 14 of body 1. Next, the guiding surface 25 of the guiding instrument's working element 24 is inclined towards the vertebral body 42 and the prosthesis is situated deep inside the intervertebral space. Deflection of the guiding surface 25 of the guiding instrument's working element 24 from the vertebral body 42, and its further inclination towards the vertebral body 42 is possible due to the swinging movement of the anchoring element 29 in a range of approximately ±4°.

Figure 21:
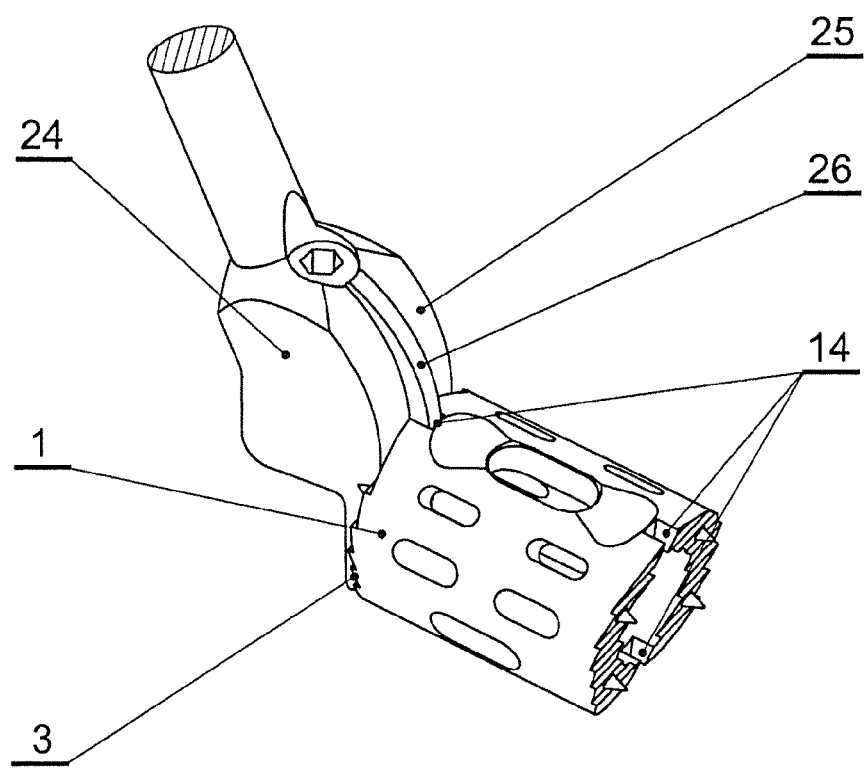
FIG. 21 is a fragmentary perspective view of the working element of the guiding instrument with the prosthesis located thereon.

FIG. 21 illustrates the guiding instrument's working element 24, its convex guiding surface 25, and the shaped guide 26 cooperating with the pair of opposite guidelines 14 located in end faces 3 of the body 1.

Figure 22:
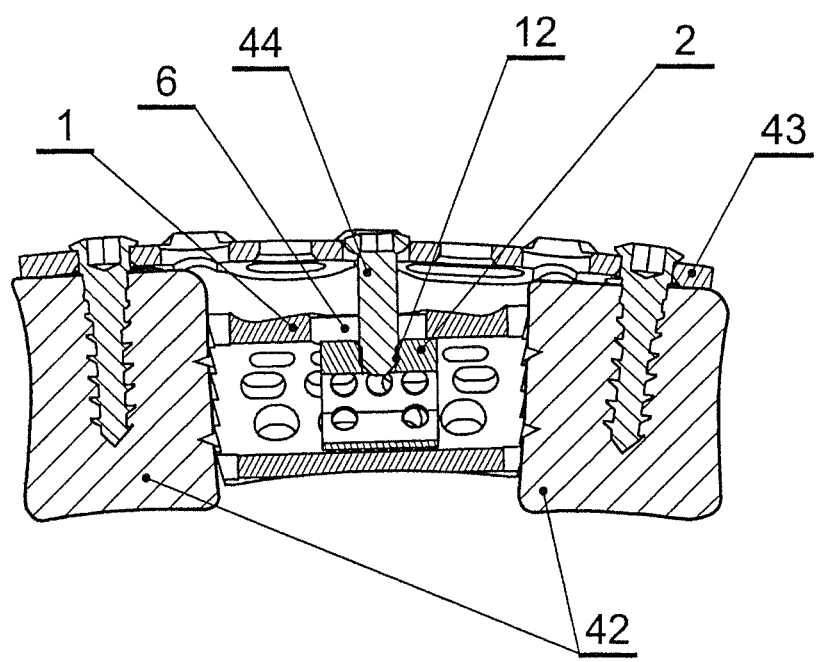
FIG. 22 is a longitudinal cross-sectional view of the prosthesis installed between two adjacent vertebrae reinforced with elements of external stabilization.

In an example of implantation of the prosthesis shown in FIG. 22, after placing the prosthesis in the intervertebral space, the prosthesis is additionally fixed with an external plate stabilizer 43 using a fixing element 44 in the form of a screw driven into the positioner's 2 hole 12 situated in the manipulative hole 6 of the body 1.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A prosthesis of an anterior spinal column comprising:
   a hollow perforated sleeve body having a wall formed about a longitudinal axis thereof and opposing end faces, wherein the body (1) is provided with overgrowth holes formed through the wall thereof and at least one anchoring element and teeth on each end face of the body (1), wherein the body (1) has in its wall at least one elongated manipulative hole (6) formed therethrough and at least one positioning hole (7), whose longitudinal axis is parallel relative to a longitudinal axis of the manipulative hole (6);
   and a positioner (2) situated within the body (1) having a wall with overgrowth holes (13) formed therein, at least one situating element (8) cooperating with the body's (1) positioning hole (7), and at least one hole (12) formed through the wall of the positioner (2), wherein the positioner (2) is slidable longitudinally along the longitudinal axis of the body (1), wherein the hole (12) is situated radially inward relative to the manipulative hole (6), wherein a portion of the positioner (2) is configured to engage with a portion of the body (1) in a manner to prevent the positioner (2) from extending outward past the end faces of the body and a total length of the prosthesis remains constant while the positioner (2) slides longitudinally within the body (1).

2. The prosthesis according to claim 1, wherein the at least one end face (3) of the body (1) is provided with at least one pair of opposite guidelines (14).

3. The prosthesis according to claim 1, wherein a part of the at least one end face (3) of the body (1) located on a same side of the body (1) as the manipulative hole (6) is deflected from a transverse axis of the body (1) at an angle not greater than 80°.

4. The prosthesis according to claim 1, wherein the wall of the body (1) is provided with at least one pair of opposite guidelines (20).

5. The prosthesis according to claim 1, wherein the positioning hole (7) is formed all the way through the wall of the body 1.

6. The prosthesis according to claim 1, wherein the positioning hole (7) is a blind hole and formed into the wall of the body (1) from its internal side.

7. The prosthesis according to claim 1, wherein the wall of the body (1) from its internal side comprises a threshold (17).

8. The prosthesis according to claim 7, wherein the threshold (17) is provided with a gap (18) formed therein.

9. The prosthesis according to claim 1, wherein the body's (1) wall from its internal side is provided with a thread (15).

10. The prosthesis according to claim 1, wherein the positioner (2) is prevented from sliding outward past the end faces of the body via the situating element (8) engaging with a boundary of the positioning hole (7).

11. The prosthesis according to claim 1, wherein the positioner (2) is a solid in a form similar to a hollowed barrel.

12. The prosthesis according to claim 1, wherein the positioner (2) is in the shape of a hollowed cylinder.

13. The prosthesis according to claim 1, wherein the positioner (2) is in the shape of a bowl.

14. The prosthesis according to claim 1, wherein the positioner (2) in a transverse section is in the shape of a polygon.

15. The prosthesis according to claim 1, wherein there is a longitudinal cut (9) in the positioner (2) forming spring arms (10).

16. The prosthesis according to claim 1, wherein the situating element (8) of the positioner (2) is a pivot.

17. The prosthesis according to claim 1, wherein the situating element (8) of the positioner (2) is a projection.

18. The prosthesis according to claim 1, wherein the situating element (8) of the positioner (2) is a pin.

19. The prosthesis according to claim 1, wherein the situating element (8) of the positioner (2) is a hole cooperating with an additional fastening element (21).

20. The prosthesis according to claim 1, wherein the situating element (8) of the positioner (2) is of a length comparable to a length of the positioner (2).

21. The prosthesis according to claim 9, wherein the wall of the positioner (2) from its external side is provided with a thread (16) cooperating with the thread (15) situated on the body's (1) wall from its internal side.

22. The prosthesis according to claim 8, wherein the positioner (2) is provided with a projection (19) cooperating with the gap (18) made in the threshold (17) of the body (1).

23. The prosthesis according to claim 1, wherein the hole (12) of positioner (2) is provided with a thread.

24. The prosthesis according to claim 1, wherein the positioner (2) is provided with an inner protrusion (11), and the hole (12) of the positioner (2) is formed through the inner protrusion.

* * * * *